(12) United States Patent
Kawahara et al.

(10) Patent No.: US 7,187,751 B2
(45) Date of Patent: Mar. 6, 2007

(54) X-RAY FLUORESCENCE SPECTROMETER AND PROGRAM USED THEREIN

(75) Inventors: Naoki Kawahara, Takatsuki (JP); Shinya Hara, Takatsuki (JP); Makoto Doi, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 11/431,604

(22) Filed: May 11, 2006

(65) Prior Publication Data

US 2006/0274882 A1    Dec. 7, 2006

(30) Foreign Application Priority Data

Jun. 7, 2005 (JP) .............................. 2005-166438

(51) Int. Cl.
*G01N 23/223* (2006.01)
(52) U.S. Cl. .......................................... 378/45; 378/46
(58) Field of Classification Search ................. 378/42, 378/44–46, 49, 50, 70, 86–90
See application file for complete search history.

(56) References Cited

U.S. PATENT DOCUMENTS 4,764,945 A * 8/1988 Abe ............................ 378/50
6,314,158 B1 * 11/2001 Shiota et al. ................. 378/48
6,668,038 B2 * 12/2003 Kataoka et al. ............... 378/45

FOREIGN PATENT DOCUMENTS

JP    2004-251785    9/2004

\* cited by examiner

*Primary Examiner*—Edward J. Glick
*Assistant Examiner*—Irakli Kiknadze
(74) *Attorney, Agent, or Firm*—Sughrue Mion, PLLC

(57) ABSTRACT

A calculating device 10 for calculating the concentration of elements contained in a sample 13 based on the FP method is provided. The calculating device 10 is operable to assume a concentration of unmeasured elements as far as unmeasured elements, of which fluorescent X-rays are not measured, are concerned, and, also, to utilize, in place of the secondary X-rays emanating from the unmeasured elements contained in the sample, scattered X-rays of the primary X-rays at least equal in number to the number of the unmeasured elements, of which concentrations are assumed, and including scattered X-rays of different wavelengths before they are scattered from the sample.

5 Claims, 2 Drawing Sheets

X-RAY FLUORESCENCE SPECTROMETER AND PROGRAM USED THEREIN

BACKGROUND OF THE INVENTION

1. Field of the Invention

The present invention relates to an X-ray fluorescence spectrometer for analyzing the composition and the area density of a sample based on the FP method and a program used therein.

2. Description of the Prior Art

The X-ray fluorescence spectrometer has hitherto been well known, which utilizes the fundamental parameter method (hereinafter referred to as "FP method") in analyzing the composition and the area density of a sample. According to the FP method, the theoretical intensity, based on the assumed concentrations of elements, the theoretical intensity of the secondary X-rays generated from elements contained in the sample is calculated and the assumed concentration of the element is successively approximately modified and calculated so that the theoretical intensity and the measured intensity measured with a detecting device can match with each other, thereby calculating the concentration of each of the elements contained in the sample. While elements such as oxygen and carbon, of which fluorescent X-rays is not measured, (i.e., the fluorescent X-rays of those elements may not be substantially measured because the intensity is low and because a considerable decay occurs as a result of absorption. Those elements are hereinafter referred to as "unmeasured elements"), are generally treated as residues, samples such as, for example, sludge, fly ash and biological specimen, which contain a large amount of unmeasured elements and of which atomic number cannot be specified, pose a problem. In this connection, there is a technique disclosed in the Japanese Patent Application No. 2004-251785.

According to this technique, as far as the unmeasured elements are concerned, the average atomic number is assumed and, using scattered X-rays as the corresponding secondary X-rays, the assumed average atomic number is successively approximately modified and calculated so that the theoretical intensity and the measured intensity can match with each other.

However, if the sample contains a unmeasured component (for example, $CH_2$) consist of a plurality of unmeasured elements (for example, C and H), and if the unmeasured component is treated as a single element with assumption of the average atomic number, the mass absorption coefficient, elastic scattering cross section, inelastic scattering cross section and so on will represent a numerical value intermediate between numerical values of two light elements having the neighboring atomic numbers and will not, in most cases, represent an actual value. As a result, the concentration of the elements in the sample cannot be accurately calculated.

In an attempt to resolve the foregoing problems, the Japanese Patent Application No. 2004-251785 referred to above discloses that as far as the unmeasured elements other than hydrogen are concerned, the average atomic number is assumed and, using scattered X-rays as the corresponding secondary X-rays, and as far as hydrogen is concerned, the concentration of the hydrogen is assumed and, using different scattered X-rays as the corresponding secondary X-rays, and that the assumed average atomic number and the assumed concentration of the hydrogen are successively approximately modified and calculated so that the theoretical intensity and the measured intensity can match with each other. However, even with those measures, the previously discussed problems are still far from being resolved. Also, because of lack of measurement information, depending on the initial value of the assumed value, the concentration of the element contained in the sample tends to converge upon the value far from the value it should have been even though the theoretical intensity and the measured intensity match with each other, resulting in a different problem in that it cannot be calculated accurately.

In other words, with the technique disclosed in the Japanese Patent Application No. 2004-251785 referred to above, it may often occur that various samples which contain a substantial amount of unmeasured elements and whose atomic number cannot be specified are incapable of being sufficiently accurately analyzed.

SUMMARY OF THE INVENTION

Accordingly, the present invention has been devised to substantially eliminate the above discussed problems and inconveniences and is intended to provide an X-ray fluorescence spectrometer for analyzing the composition and the area density of a sample based on the FP method, and a program used therein, being capable of wider application, in which various samples, which contain a substantial amount of unmeasured elements and whose atomic number cannot be specified, can be sufficiently accurately analyzed.

In order to accomplish the foregoing object of the present invention, one aspect of the present invention provides an X-ray fluorescence spectrometer which includes an X-ray source for irradiating primary X-rays towards a sample, a detecting device for measuring the intensity of secondary X-rays emanating from the sample, and a calculating device for calculating the concentration of elements contained in the sample and operable to calculate the theoretical intensity of the secondary X-rays, emanating from various elements contained in the sample, on the basis of the assumed concentration of the element and perform an optimizing calculation to determine the assumed concentration of the element so that the theoretical intensity and the intensity measured by the detecting device can match with each other. The calculating device referred to above is operable to assume concentrations of the plural unmeasured elements as far as unmeasured elements, of which fluorescent X-rays are not measured, are concerned, and, also, to utilize, in place of the secondary X-rays emanating from the unmeasured elements contained in the sample, scattered X-rays of the primary X-rays at least equal in number to the number of the unmeasured elements, of which concentrations are assumed, and including scattered X-rays of different wavelengths before they are scattered from the sample.

With the X-ray fluorescence spectrometer according to the first aspect of the present invention, since with respect to the unmeasured elements, the average atomic number is not assumed, but the concentrations of the plural unmeasured elements are assumed, the mass absorption coefficient, the elastic scattering cross section and the inelastic scattering cross section can represent an actual value. Also, since the use is made of the scattered X-rays of the primary X-rays at least equal in number to that of the unmeasured element and the scattered X-rays of the different wavelength before they are scattered by the sample are included in the scattered X-rays of the primary X-rays used, there is no possibility that the amount of information becomes insufficient. Accordingly, the various samples which contain a large amount of the unmeasured elements and of which atomic number cannot be specified can be accurately analyzed over a broad range of application.

In the X-ray fluorescence spectrometer according to the first aspect of the present invention, the calculating device is preferably of a type capable of performing an optimizing calculation by changing a combination of the unmeasured elements for which concentrations are assumed. Also, for the scattered X-rays of the primary X-rays, scattered X-rays of characteristic X-rays of the primary X-rays are preferably employed. In addition, the X-ray source preferably includes an X-ray tube and a primary beam filter capable of being selectively repositioned in a path of travel of the X-rays from the X-ray tube, in which case use is made of the primary beam filter as a transmission secondary target to thereby change the wavelength of the primary X-rays with which the sample is irradiated.

The present invention in accordance with a second aspect thereof also provides a program for enabling a computer included in the X-ray fluorescence spectrometer according to the first aspect of the present invention to function as the calculating device. Even with this program according to the second aspect of the present invention, functions and effects similar to those afforded by the X-ray fluorescence spectrometer according to the first aspect of the present invention can be obtained.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
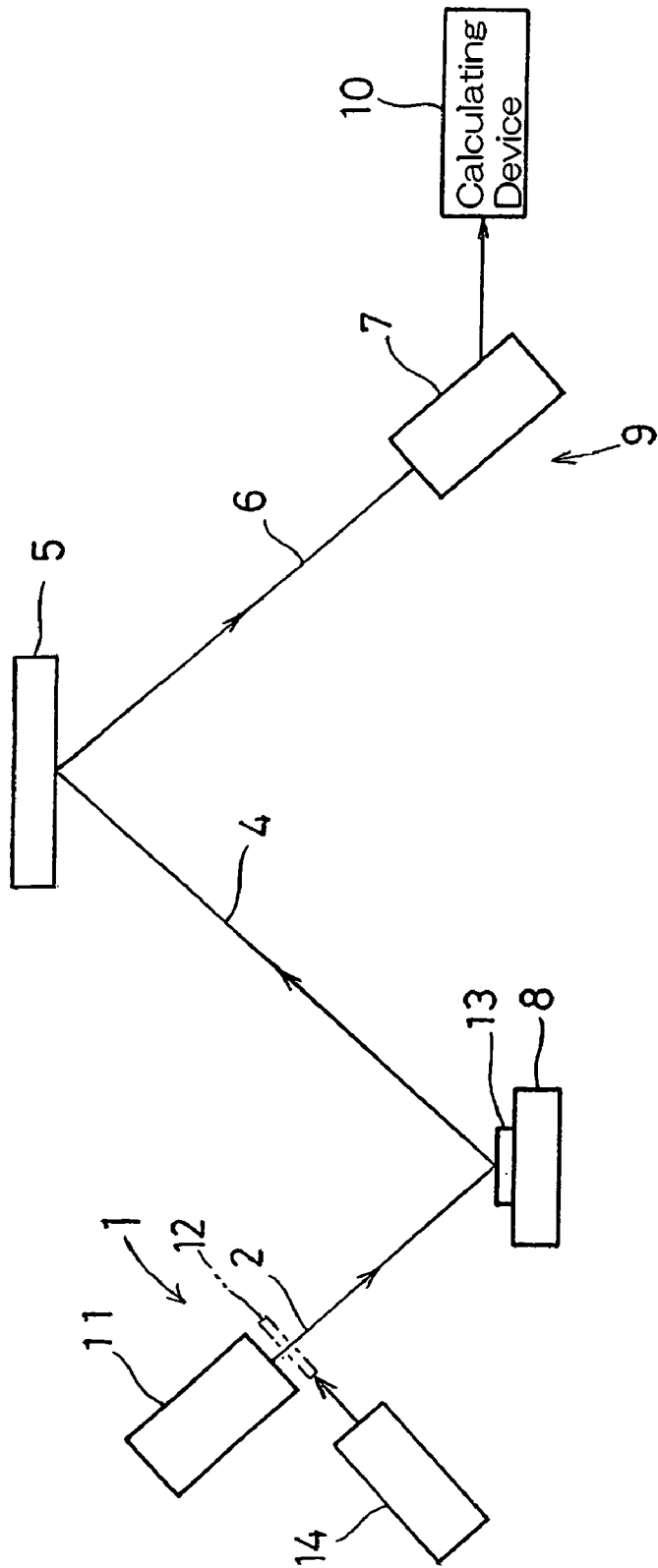
FIG. 1 is a schematic diagram showing an X-ray fluorescence spectrometer according to a preferred embodiment of the present invention.

Hereinafter, the X-ray fluorescence spectrometer according to a preferred embodiment of the present invention will be described in detail with reference to the accompanying drawings. Referring to FIG. 1, the spectrometer includes a sample stage 8 for supporting a sample 13 thereon, an X-ray source 1 for irradiating primary X-rays 2 towards the sample 13, and a detecting device 9 for measuring the intensity of secondary X-rays 4 such as fluorescent X-rays and scattered X-rays emitted from the sample 13. The detecting device 9 in turns include a spectroscopic device 5 for monochromating the secondary X-rays 4 emitted from the sample 13 and a detector 7 for measuring the intensity of each of monochromated secondary X-rays 6. It is to be noted that with no spectroscopic device 5 used, a detector having a high energy resolving power can be employed as the detecting device.

The X-ray fluorescence spectrometer of the present invention also includes a calculating device 10 for calculating the concentration of elements contained in the sample 13. The concentration of the element in the sample 13 is calculated by calculating the theoretical intensity of secondary X-rays 4, emitted from various elements contained in the sample 13, on the basis of the assumed concentration of the element and performing an optimizing calculation to determine the assumed concentration of the element so that the theoretical intensity and the intensity measured by the detecting device 9 can match with each other. With respect to unmeasured elements, of which fluorescent X-rays 4 are not measured, assumes the concentration of each of the unmeasured elements and makes use of scattered X-rays 4 of the primary X-rays at least equal in number to the number of the unmeasured elements, of which concentrations are assumed, in place of the secondary X-rays emitted from the unmeasured elements contained in the sample 13, which scattered X-rays 4 of the primary X-rays include scattered X-rays 4 having different wavelengths before they are scattered from the sample 13. In the X-ray fluorescence spectrometer of the present invention, the calculating device 10 performs an optimizing calculation by varying combination of the unmeasured elements, of which concentrations are assumed, and make use of the scattered X-rays 4 of characteristic X-rays of the primary X-rays as the scattered X-rays 4 of the primary X-rays.

The X-ray source 1 includes an X-ray tube 11 of, for example, rhodium target, a plurality of primary beam filters 12 each in the form of, for example, zirconium, and a primary beam filter changing mechanism 14 for selectively inserting and retracting the primary beam filters 12 into and from the path of travel of the X-rays emitted from the X-ray tube 11 one at a time, respectively. The primary beam filter changing mechanism 14, although schematically illustrated in FIG. 1, is of a structure including a disc having the primary beam filters 12 which have different materials or thicknesses each other mounted thereon in a row extending circumferentially thereof, and a stepping motor having a drive shaft on which the disc is mounted for rotation together therewith and is so designed that when the stepping motor is driven a certain angle, the primary beam filters 12 carried by the disc can be selectively brought into the path of travel of the X-rays between the X-ray tube 11 and the sample 13 one at a time. In addition to respective windows covered by the primary beam filters 12, the disc also has an open window, i.e., a window not covered by any of the primary beam filters 12 and, accordingly, when this open window is brought in alignment with the path between the X-ray tube 1 and the sample 13, all of the primary beam filters 12 are then retracted from such path. In other words, the primary beam filter changing mechanism 14 also has a function of selectively bringing and retracting the primary beam filters 12 into and from the path of travel of the X-rays emitted from the X-ray tube 11, respectively.

The X-ray source of the above described structure is also employed in some of the conventional X-ray fluorescence spectrometers, and the primary beam filters are exclusively employed to remove from the X-rays emitted from the X-ray tube, some of the X-rays of a wavelength unnecessary for the primary X-rays. However, in the X-ray fluorescence spectrometer of the present invention, the X-ray source 1 makes use of the primary beam filters 12 as a secondary target of a transmission type so that the wavelength of the primary X-rays to be projected onto the sample 13 may be varied. For this reason, at least one of the primary beam filters 12 contains an element that is different from the target member of the X-ray tube 11, but can be excited by the characteristic X-rays from the X-ray tube 11. By way of example, when the primary beam filter 12 including zirconium is positioned as the transmission type secondary target in the path of travel of the X-rays emitted from the X-ray tube including a rhodium target, the primary X-rays 2 projected onto the sample 13 can be varied from the characteristic X-rays including Rh-Kα line to the characteristic X-rays including Zr-Kα line.

Figure 2:
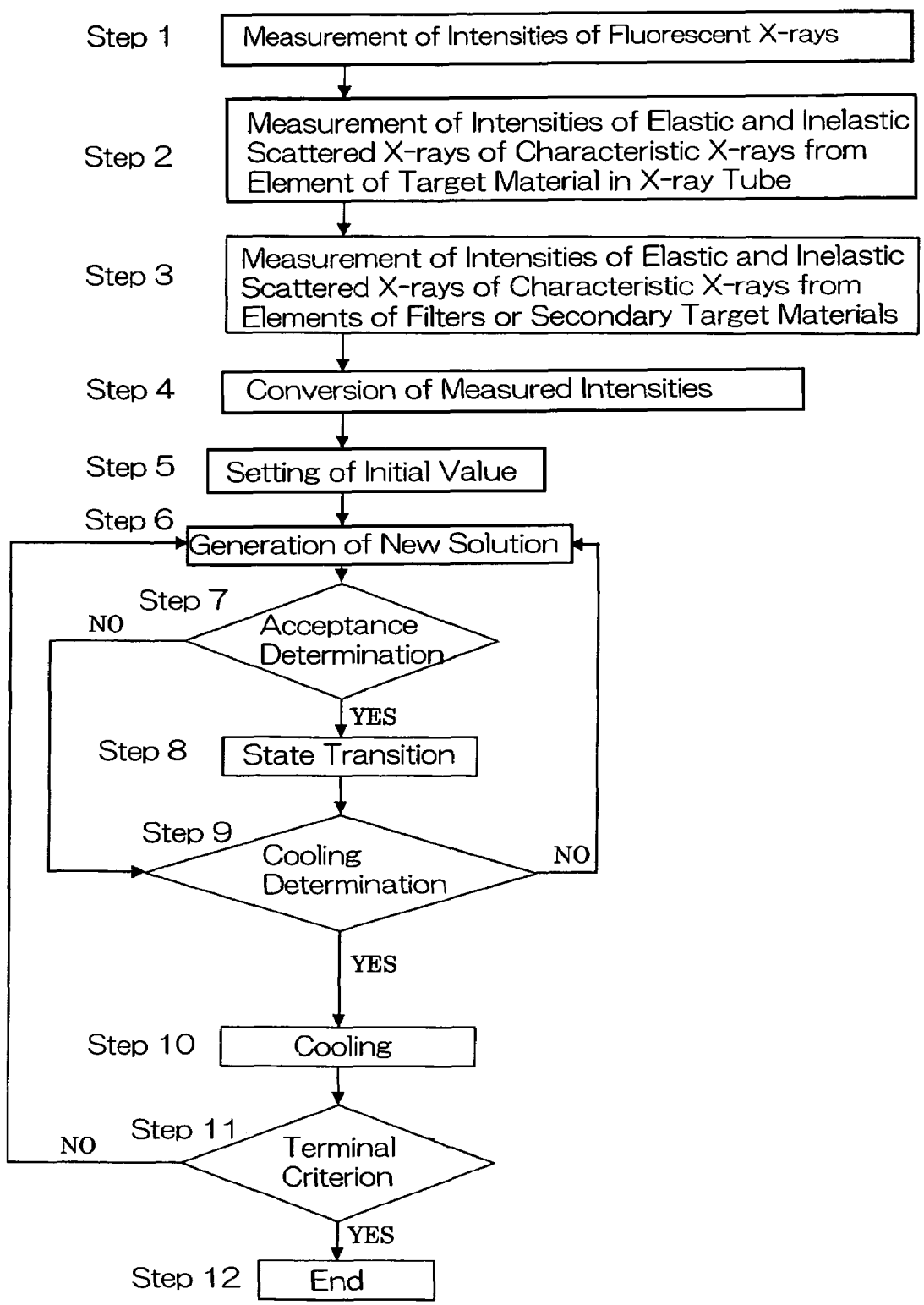
FIG. 2 is a flowchart showing the sequence of operation of the X-ray fluorescence spectrometer.

The X-ray fluorescence spectrometer of the structure described above operates in a manner represented by the flowchart shown in FIG. 2. Referring now to FIG. 2, at step 1, as the primary X-rays 2, X-rays generated by the X-ray tube 1 of, for example, a rhodium target and containing Rh-Kα line as the characteristic X-rays are irradiated from the X-ray source 1 towards the sample 13 placed on the sample table 8 shown in FIG. 1, and fluorescent X-rays 4 emanating therefrom are impinged upon the spectroscopic device 5, followed by detection of the intensity of monochromated fluorescent X-rays 6 with the detector 7. At this time, by the action of the primary beam filter changing mechanism 14, the primary beam filters 12 are retracted from the path of travel of the X-rays from the X-ray tube 11.

Then at step 2 shown in FIG. 2, in a manner similar to above, the primary X-rays 2 are irradiated towards the sample 13 shown in FIG. 1 and scattered X-rays 4 of the characteristic X-rays of the primary X-rays 2 so generated are impinged upon the spectroscopic device 5, followed by detection of the intensity of the monochromated elastic scattered X-rays 6 and that of inelastic scattered X-rays 6 with the detector 7. By way of example, the intensity of Thomson scattered X-rays of the Rh-Kα line and that of Compton scattered X-rays of the Rh-Kα are measured.

At step 3 shown in FIG. 2, by the action of the primary beam filter changing mechanism 14, the primary beam filter 12 is positioned in the path of travel of the X-rays generated from the X-ray tube 11 as a transmission secondary target, the primary X-rays 2 are irradiated towards the sample 13, and scattered X-rays 4 of the characteristic X-rays of the primary X-rays 2 so generated are impinged upon the spectroscopic device 5, followed by detection of the intensity of the monochromated elastic scattered X-rays 6 and that of inelastic scattered X-rays 6 with the detector 7. By way of example, by allowing the primary beam filter 12 including zirconium to be positioned in the path as a transmission secondary target so that the primary X-rays 2 to be irradiated towards the sample 13 can be changed to those containing Zr-Kα line as the characteristic X-rays, the intensity of Thomson scattered X-rays of the Zr-Kα line and that of Compton scattered X-rays of the Zr-Kα line are measured. Should the necessity arise, the primary beam filter 12 may be changed with that of a different material so that the intensity of the elastic scattered X-rays 6 and that of the inelastic scattered X-rays 6 of the primary X-rays 2 so generated may be measured.

It is to be noted that in order for the characteristic X-rays originating from different elements to be irradiated towards the sample as the primary X-rays, other than the use of the primary beam filter 12 as the transmission secondary target such as in the X-ray fluorescence spectrometer according to this embodiment, the use may be made of an independent transmission or reflection secondary target with no primary beam filter employed, or of an X-ray tube having a plurality of targets including different elements inside. As a matter of course, the standard X-ray tube having a single target may be provided in a plural number so that they may have different target materials. In addition, a plurality of kinds of the primary X-rays with which the sample is irradiated may not be always limited to the plural characteristic X-rays originating from different elements, but may be a plurality of kinds of characteristic X-rays of different series originating from the same element such as Rh-Kα line and Rh-Lα line since effects approximately similar to those described above can be obtained if wavelengths thereof at the time the sample is irradiated are different from each other. In such case, the use of the standard X-ray tube having a single target is sufficient and no secondary target is necessary.

As described above, the reason that the sample is irradiated with a plurality of kinds of primary X-rays, which are of different wavelengths at the time the sample is irradiated, is because in order to avoid lack of a sufficient amount of information, the scattered X-rays of the primary X-rays at least equal to the number of a plurality of unmeasured elements of which concentrations are assumed, are used for the unmeasured elements in place of the fluorescent X-rays emanating from the unmeasured elements contained in the sample, and because scattered X-rays of different wavelengths before being scattered from the sample are included in the scattered X-rays of the primary X-rays used. In this instance, for the scattered X-rays of the primary X-rays, other than the scattered X-rays of the characteristic X-rays of the primary X-rays discussed above, the scattered X-rays of continuous X-rays of the primary X-rays can be equally employed. Also, in place of the X-rays generated from the X-rays tube, X-rays, which are synchrotron radiation, can be employed.

The steps subsequent to step 3 are related to calculation performed by the calculating device 10. In the first place, at step 4 shown in FIG. 2, in order to compare each measured intensity obtained at steps 1 to 3 with the theoretical intensity, the use is made of the known conversion equation to convert into the theoretical intensity scale. Hereinafter, for the measured intensity, the measured intensity converted into the theoretical intensity scale is used. It is to be noted that in reversal thereto, the theoretical intensity may be converted into the measured intensity scale for comparison with each of the measured intensitys obtained at steps 1 to 3.

At step 5, the following initialization is performed. In the first place, predetermined candidates of unmeasured elements such as, for example, hydrogen lithium, beryllium, boron, carbon, nitrogen, oxygen, fluorine and sodium are read in. Also, the temperature $T_0$ is initialized to a predetermined value. In addition, a predetermined initial concentration (initial deposition mass) is given with respect to each of the elements, i.e., each of the measured elements, from which measured intensities of fluorescent X-rays are obtained. Yet, the unmeasured elements, of which concentrations are assumed, are extracted from the candidates that have been read in, and a predetermined initial concentration is given to each of those unmeasured elements. It is to be noted that the concentrations of the measured elements so set and the combination and concentrations of the unmeasured elements are hereinafter referred to as "state".

At step 6, a generation of new solution is carried out. In other words, starting from the current state x, the concentrations of the measured elements and the combination and concentrations of the unmeasured elements are changed to form the following state x'. At this time, the probability distribution, with which the state x' to be subsequently formed is formed from the current state x, is utilized. Where no priority is given to change of the parameters, it will be a change of equally probability. It is to be noted that although in the present invention, the use is made of the scattered X-rays of the primary X-rays at least equal in number to the unmeasured elements of which concentrations are assumed and, also, the scattered X-rays of the primary X-rays used include scattered X-rays of different wavelengths before they are scattered from the sample, the number of the unmeasured elements to be combined can be changed within the range in which the respective intensity of such plural scattered X-rays of primary X-rays can be measured. Conversely, where the atomic number of each of the unmeasured elements contained in the sample can be specified, the combination of the unmeasured elements may be left unchanged. Also, a particular unmeasured element such as, for example, hydrogen may be fixed as included necessarily in the combination.

At the step 7, an acceptance determination is carried out. In other words, using the difference $\Delta E = E' - E$ between the energy $E'$ of the subsequent state $x'$ and the energy $E$ of the current state $x$ and the temperature parameter $T$, determination is made as to whether shift to the subsequent state should be accepted. As the criterion of acceptance, the Metropolis criterion expressed by the following equation (1) is used.

$$\text{Accept}(E, E', T) = \begin{cases} 1 & \text{if } \Delta E < 0 \\ \exp\left(-\dfrac{\Delta E}{T}\right) & \text{otherwise} \end{cases} \quad (1)$$

The energy $E$ referred to above is defined by, for example, the following equation (2).

$$E = \sum_{i:\text{fluorescence}} \frac{(\textit{If}_{meas}^i - \textit{If}_{calc}^i)^2}{\sigma_i^2} + \sum_{i:\text{scattering}} \frac{(\textit{Is}_{meas}^i - \textit{Is}_{calc}^i)^2}{\sigma_i^2} \quad (2)$$

Wherein:
$\textit{If}_{meas}^i$: Measured intensity of fluorescent X-rays,
$\textit{If}_{calc}^i$: Theoretical intensity of fluorescent X-rays,
$\textit{Is}_{meas}^i$: Measured intensity of scattered X-rays,
$\textit{Is}_{calc}^i$: Theoretical intensity of scattered X-rays, and
$\sigma_i^2$: Dispersion of the measured intensity If the result of the acceptance decision is Yes, the flow goes to step 9 after step 8 at which the state transition is done, but if it is No, the flow skips step 8 and then go on to step 9.

At step 9, a cooling determination is performed. In other words, whether or not a sufficient search has been made enough to go on to the cooling is determined. More specifically, whether or not the flow on and after step 6 is repeated a predetermined number of times, whether or not the acceptance or rejection has been repeated a predetermined number of times, whether or not the acceptance is made at one time where the temperature width is sufficiently reduced, and so on are determined. If the result of the cooling decision is Yes, the flow goes to step 10, but if it is No, the flow returns to step 6.

At step 10, the cooling is carried out. In other words, the temperature is set from the current k-th temperature to the subsequent (k+1)th temperature. At this time, the following exponential annealing expressed by the following equation is employed.

$$T_{k+1} = T_0 / \log k \quad (3)$$

Then at step 11, decision is made to determine if a terminal condition is met. The halt condition may occur when the annealing is repeated a predetermined number of times, if the acceptance does not occur almost, if the same state is formed a predetermined number of times, or if change of the energy or the energy itself is sufficiently reduced down to a small value. Once the terminal condition is met, the calculation is terminated at step 12, but if it is not met, the flow returns to step 6.

In the foregoing, the optimizing calculation has been carried out by the use of the simulated annealing, but other than it, the genetic algorithm or nonlinear least squares method may be employed. Those optimizing calculations themselves are well known in the art as evidenced by the fact that the simulated annealing method itself is described in "Saitekika Riron no Kiso to Oyou (Fundamental and Application of the Optimization Theory)" published by Korona publishing company. Also, although the number of calculations increases, the successive approximation can also be carried out as is the case with the conventional FP method.

With the X-ray fluorescence spectrometer according to the foregoing embodiment of the present invention, since with respect to the unmeasured elements, the average atomic number is not assumed, but the concentrations of the plural unmeasured elements are assumed, the mass absorption coefficient, the elastic scattering cross section and the inelastic scattering cross section can represent an actual value. Also, since the use is made of the scattered X-rays of the primary X-rays at least equal in number to that of the unmeasured element and the scattered X-rays of the different wavelength before they are scattered by the sample are included in the scattered X-rays of the primary X-rays used, there is no possibility that the amount of information becomes insufficient. Accordingly, the various samples which contain a large amount of the unmeasured elements and of which atomic number cannot be specified can be accurately analyzed over a broad range of application.

Also, the X-ray fluorescence spectrometer according to the foregoing embodiment is generally equipped with a computer and, therefore, the program capable of causing the computer to function as the previously described calculating device is also included in a preferred embodiment of the present invention.

What is claimed is:

1. An X-ray fluorescence spectrometer comprising:
    an X-ray source for irradiating primary X-rays towards a sample,
    a detecting device for measuring the intensity of secondary X-rays emanating from the sample, and
    a calculating device for calculating a concentration of an element contained in the sample and operable to calculate a theoretical intensity of the secondary X-rays, emanating from various elements contained in the sample, on the basis of an assumed concentration of the element and perform an optimizing calculation to determine the assumed concentration of the element so that the theoretical intensity and an intensity measured by the detecting device can match with each other,
    wherein as far as unmeasured elements, of which fluorescent X-rays are not measured, are concerned, the calculating device is operable to assume concentrations of the plural unmeasured elements and, also, to utilize, in place of the secondary X-rays emanating from the unmeasured elements contained in the sample, scattered X-rays of the primary X-rays at least equal in number to the number of the unmeasured elements, of which concentrations are assumed, and including scattered X-rays of different wavelengths before they are scattered from the sample.

2. The X-ray fluorescence spectrometer as claimed in claim 1, wherein the calculating device performs an optimizing calculation by changing a combination of the unmeasured elements for which concentrations are assumed.

3. The X-ray fluorescence spectrometer as claimed in claim 1, wherein the scattered X-rays of the primary X-rays are scattered X-rays of characteristic X-rays of the primary X-rays.

4. The X-ray fluorescence spectrometer as claimed in claim 1, wherein the X-ray source includes an X-ray tube and a primary beam filter capable of being selectively repositioned in a path of travel of the X-rays from the X-ray tube and wherein use is made of the primary beam filter as a transmission secondary target to thereby change the wavelength of the primary X-rays with which the sample is irradiated.

5. A program for enabling a computer included in the X-ray fluorescence spectrometer, as defined in claim 1, to function as the calculating device.

* * * * *